US012781207B2

(12) United States Patent
Gordon et al.

(10) Patent No.: US 12,781,207 B2
(45) Date of Patent: Nov. 3, 2026

(54) MATERIALS AND METHODS FOR INCREASING GENE EDITING FREQUENCY

(71) Applicant: Regents of the University of Minnesota, Minneapolis, MN (US)

(72) Inventors: Wendy R. Gordon, Minneapolis, MN (US); Eric Aird, Minneapolis, MN (US); Klaus Lovendahl, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 143 days.

(21) Appl. No.: 18/815,218

(22) Filed: Aug. 26, 2024

(65) Prior Publication Data

US 2025/0051743 A1 Feb. 13, 2025

Related U.S. Application Data

(60) Division of application No. 17/810,691, filed on Jul. 5, 2022, now Pat. No. 12,071,640, which is a continuation of application No. 16/622,554, filed as application No. PCT/US2018/037353 on Jun. 13, 2018, now Pat. No. 11,421,208.

(60) Provisional application No. 62/518,960, filed on Jun. 13, 2017.

(51) Int. Cl.

| | |
|---|---|
| ***C12N 9/22*** | (2006.01) |
| ***C12N 15/11*** | (2006.01) |
| ***C12N 15/87*** | (2006.01) |

(52) U.S. Cl.
CPC ................ *C12N 9/22* (2013.01); *C12N 15/11* (2013.01); *C12N 15/87* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 11,421,208 | B2 | 8/2022 | Gordon et al. |
| 12,071,640 | B2 | 8/2024 | Gordon et al. |
| 2011/0145940 | A1 | 6/2011 | Voytas et al. |
| 2015/0167000 | A1 | 6/2015 | Voytas et al. |
| 2016/0340395 | A1 | 11/2016 | Gordon et al. |
| 2017/0058298 | A1 | 3/2017 | Kennedy et al. |
| 2019/0136210 | A1 | 5/2019 | Cotta-Ramusino et al. |
| 2020/0231952 | A1 | 7/2020 | Gordon et al. |
| 2023/0119375 | A1 | 4/2023 | Gordon et al. |

OTHER PUBLICATIONS

Anders et al., "In vitro reconstitution and crystallization of Cas9 endonuclease bound to a guide RNA and a DNA target," Methods Enzymol., 558:515-537, 2015.
Christian et al., "Targeting DNA double-strand breaks with TAL effector nucleases," Genetics, 186(2):757-761, Oct. 2010.
Cox et al., "Therapeutic genome editing: prospects and challenges," Nat. Med., 21(2):121-131, Feb. 2015.
Doudna et al., "The new frontier of genome engineering with CRISPR-Cas9," Science, 346(6213):1258096, Nov. 2014, 11 pages.
Gasiunas et al., "Cas9-crRNA ribonucleoprotein complex mediates specific DNA cleavage for adaptive immunity in bacteria," Proc. Natl. Acad. Sci. USA, 109(39):E2579-2586, Sep. 2012.
International Preliminary Report on Patentability in International Appln. No. PCT/US2018/037353, mailed on Dec. 26, 2019, 8 pages.
International Search Report & Written Opinion in International Appln. No. PCT/US2018/037353, mailed on Oct. 26, 2018, 12 pages.
Jacoby et al., "Expanding LAGLIDADG endonuclease scaffold diversity by rapidly surveying evolutionary sequence space," Nucleic Acids Res., 40(11):4954-4964, Feb. 2012.
Jinek et al., "A programmable dual-RNA-guided DNA endonuclease in adaptive bacterial immunity," Science, 337(6096):816-821, Aug. 17, 2012.
Livak et al., "Analysis of relative gene expression data using real-time quantitative PCR and the 2-ΔΔCT method, " Methods, 25(4):402-408, Dec. 2001.
Lovendahl et al., "Sequence-directed covalent protein-DNA linkages in a single step using HUH-Tags," J. Am. Chem. Soc., 139(20):7030-7035, May 8, 2017.
Mali et al., "CAS9 transcriptional activators for target specificity screening and paired nickases for cooperative genome engineering," Nat. Biotechnol., 31(9):833-838, Sep. 2013.
Pinello et al., "Analyzing CRISPR genome-editing experiments with CRISPResso," Nat. Biotechnol., 34(7):695-697, Jul. 2016.
Qi et al., "Repurposing CRISPR as an RNA-Guided Platform for Sequence-Specific Control of Gene Expression," Cell, 152(5):1173-1183, Feb. 28, 2013.
Sander et al., "Selection-free zinc-finger-nuclease engineering by context-dependent assembly (CoDA)," Nat. Methods, 8(1):67-69, Jan. 2011.
Schwinn et al., "CRISPR-Mediated Tagging of Endogenous Proteins with a Luminescent Peptide," ACS Chem. Biol., 13(2):467-474, Sep. 11, 2017.
UniProt Accession No. Q03JI6, "CRISPR-associated endonuclease Cas9 2," May 11, 2016, 4 pages.
UniProt Accession No. Q99ZW2, "CRISPR-associated endonuclease Cas9/Csn1," Jun. 8, 2016, 11 pages.

(Continued)

*Primary Examiner* — Manjunath N Rao
*Assistant Examiner* — Jae W Lee
(74) *Attorney, Agent, or Firm* — Fish & Richardson P.C.

(57) ABSTRACT

Materials and methods for gene editing using improved targeted endonucleases and endonuclease systems (e.g., Clustered Regularly Interspaced Short Palindromic Repeats (CRISPR)/CRISPR-associated protein 9 (Cas9) endonuclease systems) are provided herein.

8 Claims, 12 Drawing Sheets

Specification includes a Sequence Listing.

(56) References Cited

OTHER PUBLICATIONS

Zhang et al., "High frequency targeted mutagenesis in *Arabidopsis thaliana* using zinc finger nucleases," Proc. Natl. Acad. Sci. USA, 107(26):12028-12033, Jun. 29, 2010.
Zuris et al., "Cationic lipid-mediated delivery of proteins enables efficient protein-based genome editing in vitro and in vivo," Nat. Biotechnol., 33(1):73-80, Jan. 2015.

| Primer pair | Slope | Efficiency |
|---|---|---|
| GAPDH | -3.265 | 102% |
| HiBiT | -3.343 | 99% |

FIG. 6B

| DNA source | Target | $C_T$ | Average $C_T$ |
|---|---|---|---|
| Cas9 | GAPDH | 21.89<br>21.93<br>22.00 | 21.94±0.06 |
| | HiBiT | 25.77<br>25.54<br>24.64 | 25.32±0.60 |
| Cas9-PCV | GAPDH | 22.17<br>22.00<br>22.05 | 22.07±0.09 |
| | HiBiT | 24.52<br>24.52<br>24.34 | 24.46±0.10 |

Change in HDR with Cas9-PCV: 1.98 fold*

* Ratio calculated using Pfaffl Method where *GAPDH* is the reference

SEQUENCE LISTING

```
Sequence total quantity: 24
SEQ ID NO: 1           moltype = AA  length = 116
FEATURE                Location/Qualifiers
source                 1..116
                       mol_type = protein
                       organism = Porcine circovirus 2
SEQUENCE: 1
SPSKKNGRSG PQPHKRWVFT LNNPSEDERK KIRDLPISLF DYFIVGEEGN EEGRTPHLQG  60
FANFVKKQTF NKVKWYLGAR CHIEKAKGTD QQNKEYCSKE GNLLMECGAP RSQGQR      116

SEQ ID NO: 2           moltype = AA  length = 340
FEATURE                Location/Qualifiers
source                 1..340
                       mol_type = protein
                       organism = Bacteriophage PhiX174
SEQUENCE: 2
KSRRGFAIQR LMNAMRQAHA DGWFIVFDTL TLADDRLEAF YDNPNALRDY FRDIGRMVLA  60
AEGRKANDSH ADCYQYFCVP EYGTANGRLH FHAVHFMRTL PTGSVDPNFG RRVRNRRQLN  120
SLQNTWPYGH SMPIAVRYTQ DAFSRSGWLW PVDAKGEPLK ATSYMAVGFY VAKYVNKKSD  180
MDLAAKGLGA KEWNNSLKTK LSLLPKKLFR IRMSRNFGMK MLTMTNLSTE CLIQLTKLGY  240
DATPFNQILK QNAKREMRLR LGKVTVADVL AAQPVTTNLL KFMRASIKMI GVSNLQSFIA  300
SMTQKLTLSD ISDESKNYLD KAGITTACLR IKSKWTAGGK                        340

SEQ ID NO: 3           moltype = AA  length = 186
FEATURE                Location/Qualifiers
source                 1..186
                       mol_type = protein
                       organism = Escherichia coli
SEQUENCE: 3
MAIYHLTAKT GSRSGGQSAR AKADYIQREG KYARDMDEVL HAESGHMPEF VERPADYWDA  60
ADLYERANGR LFKEVEFALP VELTLDQQKA LASEFAQHLT GAERLPYTLA IHAGGGENPH  120
CHLMISERIN DGIERPAAQW FKRYNGKTPE KGGAQKTEAL KPKAWLEQTR EAWADHANRA  180
LERAGH                                                             186

SEQ ID NO: 4           moltype = AA  length = 330
FEATURE                Location/Qualifiers
source                 1..330
                       mol_type = protein
                       organism = Escherichia coli
SEQUENCE: 4
MMSIAQVRSA GSAGNYYTDK DNYYVLGSMG ERWAGRGAEQ LGLQGSVDKD VFTRLLEGRL  60
PDGADLSRMQ DGSNRHRPGY DLTFSAPKSV SMMAMLGGDK RLIDAHNQAV DFAVRQVEAL  120
ASTRVMTDGQ SETVLTGNLV MALFNHDTSR DQEPQLHTHA VVANVTQHNG EWKTLSSDKV  180
GKTGFIENVY ANQIAFGRLY REKLKEQVEA LGYETEVVGK HGMWEMPGVP VEAFSGRSQT  240
IREAVGEDAS LKSRDVAALD TRKSKQHVDP EIKMAEWMQT LKETGFDIRA YRDAADQRAD  300
LRTLTPGPAS QDGPDVQQAV TQAIAGLSER                                   330

SEQ ID NO: 5           moltype = AA  length = 133
FEATURE                Location/Qualifiers
source                 1..133
                       mol_type = protein
                       organism = Streptococcus agalactiae
SEQUENCE: 5
MAKEKARYFT FLLYPESIPS DWELKLETLG VPMAISPLHD KDKSSIKGQK YKKAHYHVLY  60
IAKNPVTADS VRKKIKLLLG EKSLAMVQVV LNVENMYLYL THESKDAIAK KKHVYDKADI  120
KLINNFDIDR YLE                                                     133

SEQ ID NO: 6           moltype = AA  length = 130
FEATURE                Location/Qualifiers
source                 1..130
                       mol_type = protein
                       organism = Streptococcus pneumoniae
SEQUENCE: 6
MSEKKEIVKG RDWTFLVYPE SAPENWRTIL DETFMRWVES PLHDKDVNAD GEIKKPHWHI  60
LLSSDGPITQ TAVQKIIGPL NCPNAQKVGS AKGLVRYMVH LDNPEKYQYS LDEIVGHNGA  120
DVASYFELTA                                                         130

SEQ ID NO: 7           moltype = AA  length = 98
FEATURE                Location/Qualifiers
source                 1..98
                       mol_type = protein
                       organism = Faba bean necrotic yellows virus
SEQUENCE: 7
MARQVICWCF TLNNPLSPLS LHDSMKYLVY QTEQGEAGNI HFQGYIEMKK RTSLAGMKKL  60
IPGAHFEKRR GTQGEARAYS MKEDTRLEGP WEYGEFVP                          98

SEQ ID NO: 8           moltype = AA  length = 219
FEATURE                Location/Qualifiers
```

-continued

```
source                 1..219
                       mol_type = protein
                       organism = Staphylococcus aureus
SEQUENCE: 8
AMYHFQNKFV SKANGQSATA KSAYNSASRI KDFKENEFKD YSNKQCDYSE ILLPNNADDK  60
FKDREYLWNK VHDVENRKNS QVAREIIIGL PNEFDPNSNI ELAKEFAESL SNEGMIVDLN  120
IHKINEENPH AHLLCTLRGL DKNNEFEPKR KGNDYIRDWN TKEKHNEWRK RWENVQNKHL  180
EKNGFSVRVS ADSYKNQNID LEPTKKEGWK ARKFEDETG                        219

SEQ ID NO: 9           moltype = AA  length = 293
FEATURE                Location/Qualifiers
source                 1..293
                       mol_type = protein
                       organism = Escherichia coli
SEQUENCE: 9
MLSHMVLTRQ DIGRAASYYE DGADDYYAKD GDASEWQGKG AEELGLSGEV DSKRFRELLA  60
GNIGEGHRIM RSATRQDSKE RIGLDLTFSA PKSVSLQALV AGDAEIIKAH DRAVARTLEQ  120
AEARAQARQK IQGKTRIETT GNLVIGKFRH ETSRERDPQL HTHAVILNMT KRSDGQWRAL  180
KNDEIVKATR YLGAVYNAEL AHELQKLGYQ LRYGKDGNFD LAHIDRQQIE GFSKRTEQIA  240
EWYAARGLDP NSVSLEQKQA AKVLSRAKKT SVDREALRAE WQATAKELGI DFS         293

SEQ ID NO: 10          moltype = AA  length = 257
FEATURE                Location/Qualifiers
source                 1..257
                       mol_type = protein
                       organism = Agrobacterium tumefaciens
SEQUENCE: 10
MPDRAQVIIR IVPGGGTKTL QQIINQLEYL SRKGRLELQR SARHLDIPLP PDQIHELARS  60
WVQETGTYDE SQPDEERQQE LTTHIIVSFP AGTSQVAAYA ASREWAAEMF GSGAGGGRYN  120
YLTAFHIDRD HPHLHVVVNR RELLGHGWLK ISRRHPQLNY DALRIKMAEI SLRHGIALDA  180
SRRAERGITE RPITYAQYRR LEREQARQIR FEDADLEQSS PQGDHPEFSQ PFDTSPFEAS  240
AGGPEDMPRP NNRQNES                                                257

SEQ ID NO: 11          moltype = AA  length = 120
FEATURE                Location/Qualifiers
source                 1..120
                       mol_type = protein
                       organism = Tomato yellow leaf curl virus
SEQUENCE: 11
MPRLFKIYAK NYFLTYPNCS LSKEEALSQL KKLETPTNKK YIKVCKELHE NGEPHLHVLI  60
QFEGKYQCKN QRFFDLVSPN RSAHFHPNIQ AAKSSTDVKT YVEKDGNFID FGVSQIDGRS  120

SEQ ID NO: 12          moltype = AA  length = 130
FEATURE                Location/Qualifiers
source                 1..130
                       mol_type = protein
                       organism = Streptococcus pneumoniae
SEQUENCE: 12
MSEKKEIVKG RDWTFLVYPE SAPENWRTIL DETFMRWVES PLHDKDVNAD GEIKKPHWHI  60
LLSSDGPITQ TAVQKIIGPL NCPNAQKVGS AKGLVRYMVH LDNPEKYQYS LDEIVGHNGA  120
DVASYFELTA                                                        130

SEQ ID NO: 13          moltype = AA  length = 111
FEATURE                Location/Qualifiers
source                 1..111
                       mol_type = protein
                       organism = Duck circovirus
SEQUENCE: 13
MAKSGNYSYK RWVFTINNPT FEDYVHVLEF CTLDNCKFAI VGEEKGANGT PHLQGFLNLR  60
SNARAAALEE SLGGRAWLSR ARGSDEDNEE YCAKESTYLR VGEPVSKGRS S           111

SEQ ID NO: 14          moltype = AA  length = 1388
FEATURE                Location/Qualifiers
source                 1..1388
                       mol_type = protein
                       organism = Streptococcus thermophilus
SEQUENCE: 14
MTKPYSIGLD IGTNSVGWAV TTDNYKVPSK KMKVLGNTSK KYIKKNLLGV LLFDSGITAE  60
GRRLKRTARR RYTRRRNRIL YLQEIFSTEM ATLDDAFFQR LDDSFLVPDD KRDSKYPIFG  120
NLVEEKAYHD EFPTIYHLRK YLADSTKKAD LRLVYLALAH MIKYRGHFLI EGEFNSKNND  180
IQKNFQDFLD TYNAIFESDL SLENSKQLEE IVKDKISKLE KKDRILKLFP GEKNSGIFSE  240
FLKLIVGNQA DFRKCFNLDE KASLHFSKES YDEDLETLLG YIGDDYSDVF LKAKKLYDAI  300
LLSGFLTVTD NETEAPLSSA MIKRYNEHKE DLALLKEYIR NISLKTYNEV FKDDTKNGYA  360
GYIDGKTNQE DFYVYLKKLL AEFEGADYFL EKIDREDFLR KQRTFDNGSI PYQIHLQEMR  420
AILDKQAKFY PFLAKNKERI EKILTFRIPY YVGPLARGNS DFAWSIRKRN EKITPWNFED  480
VIDKESSAEA FINRMTSFDL YLPEEKVLPK HSLLYETFNV YNELTKVRFI AESMRDYQFL  540
DSKQKKDIVR LYFKDKRKVT DKDIIEYLHA IYGYDGIELK GIEKQFNSSL STYHDLLNII  600
NDKEFLDDSS NEAIIEEIIH TLTIFEDREM IKQRLSKFEN IFDKSVLKKL SRRHYTGWGK  660
LSAKLINGIR DEKSGNTILD YLIDDGISNR NFMQLIHDDA LSFKKKIQKA QIIGDEDKGN  720
```

-continued

```
IKEVVKSLPG SPAIKKGILQ SIKIVDELVK VMGGRKPESI VVEMARENQY TNQGKSNSQQ  780
RLKRLEKSLK ELGSKILKEN IPAKLSKIDN NALQNDRLYL YYLQNGKDMY TGDDLDIDRL  840
SNYDIDHIIP QAFLKDNSID NKVLVSSASN RGKSDDVPSL EVVKKRKTFW YQLLKSKLIS  900
QRKFDNLTKA ERGGLSPEDK AGFIQRQLVE TRQITKHVAR LLDEKFNNKK DENNRAVRTV  960
KIITLKSTLV SQFRKDFELY KVREINDFHH AHDAYLNAVV ASALLKKYPK LEPEFVYGDY  1020
PKYNSFRERK SATEKVYFYS NIMNIFKKSI SLADGRVIER PLIEVNEETG ESVWNKESDL  1080
ATVRRVLSYP QVNVVKKVEE QNHGLDRGKP KGLFNANLSS KPKPNSNENL VGAKEYLDPK  1140
KYGGYAGISN SFTVLVKGTI EKGAKKKITN VLEFQGISIL DRINYRKDKL NFLLEKGYKD  1200
IELIIELPKY SLFELSDGSR RMLASILSTN NKRGEIHKGN QIFLSQKFVK LLYHAKRISN  1260
TINENHRKYV ENHKKEFEEL FYYILEFNEN YVGAKKNGKL LNSAFQSWQN HSIDELCSSF  1320
IGPTGSERKG LFELTSRGSA ADFEFLGVKI PRYRDYTPSS LLKDATLIHQ SVTGLYETRI  1380
DLAKLGEG                                                          1388

SEQ ID NO: 15          moltype = AA  length = 1368
FEATURE                Location/Qualifiers
source                 1..1368
                       mol_type = protein
                       organism = Streptococcus pyogenes
SEQUENCE: 15
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 16          moltype = AA  length = 1616
FEATURE                Location/Qualifiers
REGION                 1..1616
                       note = synthetic polypeptide
source                 1..1616
                       mol_type = protein
                       organism = synthetic construct
SEQUENCE: 16
MRGSHHHHHH MASGSDSEVN QEAKPEVKPE VKPETHINLK VSDGSSEIFF KIKKTTPLRR  60
LMEAFAKRQG KEMDSLRFLY DGIRIQADQT PEDLDMEDND IIEAHREQIG GSMDKKYSIG  120
LDIGTNSVGW AVITDEYKVP SKKFKVLGNT DRHSIKKNLI GALLFDSGET AEATRLKRTA  180
RRRYTRRKNR ICYLQEIFSN EMAKVDDSFF HRLEESFLVE EDKKHERHPI FGNIVDEVAY  240
HEKYPTIYHL RKKLVDSTDK ADLRLIYLAL AHMIKFRGHF LIEGDLNPDN SDVDKLFIQL  300
VQTYNQLFEE NPINASGVDA KAILSARLSK SRRLENLIAQ LPGEKKNGLF GNLIALSLGL  360
TPNFKSNFDL AEDAKLQLSK DTYDDDLDNL LAQIGDQYAD LFLAAKNLSD AILLSDILRV  420
NTEITKAPLS ASMIKRYDEH HQDLTLLKAL VRQQLPEKYK EIFFDQSKNG YAGYIDGGAS  480
QEEFYKFIKP ILEKMDGTEE LLVKLNREDL LRKQRTFDNG SIPHQIHLGE LHAILRRQED  540
FYPFLKDNRE KIEKILTFRI PYYVGPLARG NSRFAWMTRK SEETITPWNF EEVVDKGASA  600
QSFIERMTNF DKNLPNEKVL PKHSLLYEYF TVYNELTKVK YVTEGMRKPA FLSGEQKKAI  660
VDLLFKTNRK VTVKQLKEDY FKKIECFDSV EISGVEDRFN ASLGTYHDLL KIIKDKDFLD  720
NEENEDILED IVLTLTLFED REMIEERLKT YAHLFDDKVM KQLKRRRYTG WGRLSRKLIN  780
GIRDKQSGKT ILDFLKSDGF ANRNFMQLIH DDSLTFKEDI QKAQVSGQGD SLHEHIANLA  840
GSPAIKKGIL QTVKVVDELV KVMGRHKPEN IVIEMARENQ TTQKGQKNSR ERMKRIEEGI  900
KELGSQILKE HPVENTQLQN EKLYLYYLQN GRDMYVDQEL DINRLSDYDV DHIVPQSFLK  960
DDSIDNKVLT RSDKNRGKSD NVPSEEVVKK MKNYWRQLLN AKLITQRKFD NLTKAERGGL  1020
SELDKAGFIK RQLVETRQIT KHVAQILDSR MNTKYDENDK LIREVKVITL KSKLVSDFRK  1080
DFQFYKVREI NNYHHAHDAY LNAVVGTALI KKYPKLESEF VYGDYKVYDV RKMIAKSEQE  1140
IGKATAKYFF YSNIMNFFKT EITLANGEIR KRPLIETNGE TGEIVWDKGR DFATVRKVLS  1200
MPQVNIVKKT EVQTGGFSKE SILPKRNSDK LIARKKDWDP KKYGGFDSPT VAYSVLVVAK  1260
VEKGKSKKLK SVKELLGITI MERSSFEKNP IDFLEAKGYK EVKKDLIIKL PKYSLFELEN  1320
GRKRMLASAG ELQKGNELAL PSKYVNFLYL ASHYEKLKGS PEDNEQKQLF VEQHKHYLDE  1380
IIEQISEFSK RVILADANLD KVLSAYNKHR DKPIREQAEN IIHLFTLTNL GAPAAFKYFD  1440
TTIDRKRYTS TKEVLDATLI HQSITGLYET RIDLSQLGGD GGGSGTRLPK KKRKVGGGSG  1500
SPSKKNGRSG PQPHKRWVFT LNNPSEDERK KIRDLPISLF DYFIVGEEGN EEGRTPHLQG  1560
FANFVKKQTF NKVKWYLGAR CHIEKAKGTD QQNKEYCSKE GNLLMECGAP RSQGQR      1616
```

```
SEQ ID NO: 17          moltype = DNA  length = 21
FEATURE                Location/Qualifiers
misc_feature           1..21
                       note = synthetic oligonucleotide
source                 1..21
                       mol_type = other DNA
                       organism = synthetic construct
SEQUENCE: 17
ctcccacctt tctcatccaa g                                        21

SEQ ID NO: 18          moltype = DNA  length = 19
FEATURE                Location/Qualifiers
misc_feature           1..19
                       note = synthetic oligonucleotide
source                 1..19
                       mol_type = other DNA
                       organism = synthetic construct
SEQUENCE: 18
acatcacccc tctacctcc                                           19

SEQ ID NO: 19          moltype = DNA  length = 22
FEATURE                Location/Qualifiers
misc_feature           1..22
                       note = synthetic oligonucleotide
source                 1..22
                       mol_type = other DNA
                       organism = synthetic construct
SEQUENCE: 19
gagactggct cttaaaaagt gc                                       22

SEQ ID NO: 20          moltype = DNA  length = 21
FEATURE                Location/Qualifiers
misc_feature           1..21
                       note = synthetic oligonucleotide
source                 1..21
                       mol_type = other DNA
                       organism = synthetic construct
SEQUENCE: 20
gctaatcttc ttgaacagcc g                                        21

SEQ ID NO: 21          moltype = DNA  length = 22
FEATURE                Location/Qualifiers
misc_feature           1..22
                       note = synthetic oligonucleotide
source                 1..22
                       mol_type = other DNA
                       organism = synthetic construct
SEQUENCE: 21
ctgacaactc ttttcatctt ct                                       22

SEQ ID NO: 22          moltype = DNA  length = 18
FEATURE                Location/Qualifiers
misc_feature           1..18
                       note = synthetic oligonucleotide
source                 1..18
                       mol_type = other DNA
                       organism = synthetic construct
SEQUENCE: 22
aaagtgcagg gtctggcg                                            18

SEQ ID NO: 23          moltype = DNA  length = 22
FEATURE                Location/Qualifiers
misc_feature           1..22
                       note = synthetic oligonucleotide
source                 1..22
                       mol_type = other DNA
                       organism = synthetic construct
SEQUENCE: 23
atgagcttgc tcctcccaaa cc                                       22

SEQ ID NO: 24          moltype = DNA  length = 22
FEATURE                Location/Qualifiers
misc_feature           1..22
                       note = synthetic oligonucleotide
```

-continued

```
source                 1..22
                       mol_type = other DNA
                       organism = synthetic construct
SEQUENCE: 24
tcactactta ccttgctgga cc                                    22
```

MATERIALS AND METHODS FOR INCREASING GENE EDITING FREQUENCY

CROSS-REFERENCE TO RELATED APPLICATIONS

This application is a divisional of U.S. application Ser. No. 17/810,691, filed Jul. 5, 2022, which is a continuation of U.S. application Ser. No. 16/622,554, filed on Dec. 13, 2019, now U.S. Pat. No. 11,421,208, which is a National Stage application under 35 U.S.C. § 371 of International Application No. PCT/US2018/037353, having an International Filing Date of Jun. 13, 2018, which claims benefit of priority from U.S. Provisional Application Ser. No. 62/518,960, filed on Jun. 13, 2017. The disclosures of the prior applications are considered part of (and are incorporated by reference in) the disclosure of this application.

STATEMENT AS TO FEDERALLY SPONSORED RESEARCH

This invention was made with government support under GM119483 awarded by the National Institutes of Health. The government has certain rights in the invention.

SEQUENCE LISTING

This application includes a sequence listing that has been submitted electronically as an XML file named 09531-0376003_SL_ST26.xml. The XML file, created on Jan. 9, 2023, is 32,253 bytes in size. The material in the XML file is hereby incorporated by reference in its entirety.

TECHNICAL FIELD

This document relates to improved materials and methods for gene editing using endonucleases and endonuclease systems, such as the Clustered Regularly Interspaced Short Palindromic Repeats (CRISPR)/CRISPR-associated protein 9 (Cas9) endonuclease system. For example, the methods provided herein include the use of a tag to couple a donor nucleic acid sequence to a CRISPR/Cas9 complex, thus increasing the efficiency with which the donor nucleic acid is transferred into a targeted sequence.

BACKGROUND

Gene editing can be used to generate various types of targeted mutations within the genome of cells, including mutations to correct point mutations, mutations to knock-out or knock-in aberrant protein function, and mutations to introduce coding or noncoding regions of the genome where they are lacking. The CRISPR/Cas9 system provides a versatile and powerful tool for editing the genome at virtually any point by first introducing a double strand break or single strand nick at a specific site (via the Cas9 enzyme and a specially designed guide RNA), and then allowing DNA repair mechanisms to (1) rejoin the two ends in a process called Non-homologous End Joining (NHEJ), which can disrupt the gene by introducing a stop codon or a frameshift mutation, or (2) insert a region of DNA (donor DNA) containing modifications of interest (e.g., point mutations, insertions of sequences such as epitope tags, or deletions) via a process called Homology Directed Repair (HDR). A donor DNA can be, for example, a single strand oligonucleotide, a plasmid, or linearized DNA; the donor DNA can be transfected or electroporated into cells along with one or more plasmids containing the Cas9 and the guide RNA (gRNA) or with a preassembled recombinant Cas9 protein/gRNA complex (Livak and Schmittgen *Methods* 25(4):402-408, 2001). The HDR editing process tends to be inefficient compared to the formation of DNA nicks/breaks, however, perhaps because the competing pathway of NHEJ is more efficient than the delivery and integration of donor DNA.

SUMMARY

This document is based, at least in part, on the discovery that a Cas9 enzyme can be fused to an HUH tag, thereby allowing covalent tethering of a donor DNA molecule to a Cas9-HUH/gRNA complex, and providing a means for delivery, to a target nucleotide sequence, of a single complex containing all the components required for DNA cleavage and HDR. The enhanced bio-availability of donor DNA at sites of Cas9 activity may enhance the efficiency of gene editing, overcoming a substantial hurdle in using gene-editing for disease therapy.

Thus, in a first aspect, this document features a method for modifying the genetic material of a cell, where the method includes introducing into the cell a ribonucleic acid protein (RNP) complex, where the RNP complex contains (a) a polypeptide including a Cas9 endonuclease and an HUH tag, (b) a guide RNA targeted to a selected sequence in the genome of the cell, and (c) a donor DNA containing a single-stranded target sequence that can specifically interact with the HUH tag, wherein, after the introducing, the guide RNA directs the RNP complex to the selected sequence, the Cas9 endonuclease induces a nick or a double strand break at or near the selected sequence, and the donor DNA is inserted at the double stranded break. The polypeptide can include a linker between the Cas9 endonuclease and the HUH tag. The HUH tag can be at the N-terminus of the Cas9 endonuclease polypeptide, or at the C-terminus of the Cas9 endonuclease polypeptide. The Cas9 endonuclease can contain one or more mutations as compared to the Cas9 endonuclease having the amino acid sequence set forth in SEQ ID NO:14 or SEQ ID NO:15. The one or more mutations can reduce the endonuclease activity of the Cas9, reduce non-specific activity of the Cas9, or cause the Cas9 polypeptide to have nickase activity rather than double strand cleavage activity. The method can include introducing the RNP complex into the cell using a cationic lipid, electroporation, or injection. The RNP complex can be attached to an antibody, a nanobody, or an ScFv that binds to a cell-surface antigen of the cell, or can be attached to a gold nanoparticle or a cell-penetrating polypeptide.

In another aspect, this document features a fusion polypeptide comprising a Cas9 polypeptide and an HUH tag. The polypeptide can further include a linker (e.g., a linker positioned between the Cas9 polypeptide and the HUH tag). The HUH tag can be fused to the N-terminus of Cas9, or to the C-terminus of Cas9. The Cas9 polypeptide can include mutations that disable its catalytic activity, reduce non-specific cutting, or cause it to nick instead of induce a double strand break.

In another aspect, this document features a RNP molecular complex. In general, this complex can include a recombinant Cas9/HUH tag fusion polypeptide, a gRNA that recognizes a specific site in the genome of a cell, and a piece of DNA containing a single-stranded target sequence recognized by the HUH tag. The DNA can be, for example, an oligonucleotide [e.g., a single-stranded oligodeoxynucleotide (ssODN)] or a PCR product with a single-strand overhang generated by incorporating a spacer nucleotide into the PCR product, which a polymerase cannot read through. In some embodiments, a ssODN can be annealed to a complementary oligonucleotide that is covalently attached to the HUH tag. The DNA can include one or more "homology arms," sequences with homology to a genomic sequence near the sequence recognized by the gRNA. The DNA can include a linker between the HUH tag target sequence and the homology arms (e.g., on the ssODN) or other DNA, and the linker can be varied.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A: SDS-PAGE showing Nickel affinity purification of the Cas9 and Cas9-PCV proteins. The lanes labeled Cas9 and Cas9-PCV on the right side of the gels show the elution fractions of the protein from the Nickel columns. FIG. 1B: SDS-PAGE gel showing cation exchange purification after nickel affinity purification. The Cas9 and Cas9-PCV proteins are the dominant species, demonstrating that the two-step purification produced high-quality protein.

FIG. 4 shows that covalent tethering resulted in a 2- to 3-fold increase in incorporation of the luciferase tag (HiBIT; Promega). This effect was only observed when the PCV target was present on the ssODN.

As shown in FIG. 5A, enhancements up to 3-fold were observed when 1.5 or 3 pmol Cas9-PCV was used. Enhancements up to about 30-fold were observed when lower concentrations of RNP were used (FIG. 5B).

FIGS. 6A, 6B, and 6C show that covalent tethering of the donor DNA enhanced HDR when assayed at the DNA level. Quantitative polymerase chain reaction (qPCR; also referred to as real-time PCR) was performed on cell lysates from FIG. 5 with two sets of primers—a GAPDH set that annealed to unmodified GAPDH, and a HiBIT set that annealed to luciferase-tag modified GAPDH. FIG. 6A is a graph showing that the amplification efficiencies of the primers were equivalent, meaning that cycle threshold values could be compared. The cycle threshold times are shown in FIG. 6B for triplicate measurements for both sets of primers for PCV or PCV-Cas9. The cycle threshold values were used to calculate the relative incorporation of HiBIT into GAPDH. A two-fold enhancement of HDR efficiency was calculated (FIG. 6C), demonstrating that covalent tethering of the donor DNA to Cas9-PCV enhanced HDR.

DETAILED DESCRIPTION

Figure 1A:
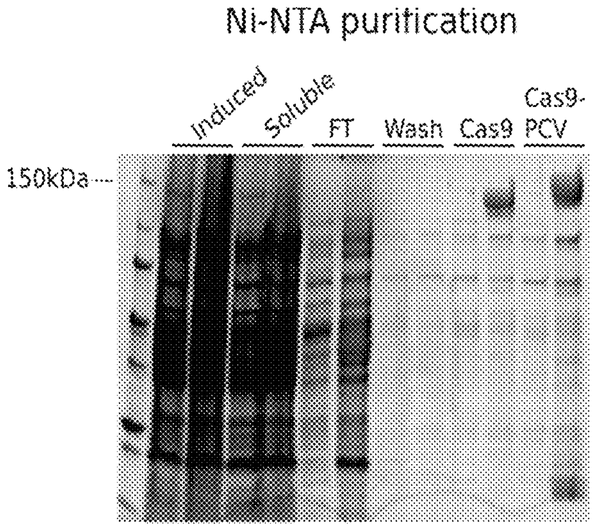
FIGS. 1A and 1B are images of sodium dodecyl sulfate polyacrylamide gel electrophoresis (SDS-PAGE) gels demonstrating expression and purification of PCV2-Cas9 fusions from *E. coli*.

As described herein, a tag that can form covalent links with single-stranded DNA, referred to herein as an HUH tag, can be fused to a targeted endonuclease (e.g., a Cas9 endonuclease) in order to allow for covalent tethering (via the HUH tag) of a donor DNA to the endonuclease or, in the case of Cas9, to the Cas9/gRNA complex, thus permitting delivery into cells of a single complex containing all components required for DNA cleavage and HDR. Enhanced availability of donor DNA at sites of endonuclease activity can greatly enhance the efficiency of gene editing, overcoming a substantial hurdle in using gene editing for disease therapy. Other potential applications of HUH tagged endonuclease fusions also are contemplated, including the use of such fusions to specifically tag the genome with bright fluorophores incorporated into DNA oligonucleotides that are covalently linked to the HUH tag coupled to a catalytically-dead endonuclease (e.g., a catalytically dead Cas9 combined with a gRNA such as a single-guide RNA (sgRNA) for directing the Cas9 to a specific sequence).

Thus, this document provides fusion polypeptides containing an endonuclease (e.g., a Cas9 endonuclease) and an HUH tag. In addition, this document provides nucleic acids encoding the fusion polypeptides, and methods for using the polypeptides and/or nucleic acids to achieve modify the genomic DNA within a cell.

The term "polypeptide" as used herein refers to a compound of two or more subunit amino acids, regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from cellular components with which it normally is found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

The terms "nucleic acid" and "polynucleotide" can be used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The nucleic acids may be incorporated into or contained within recombinant nucleic acid constructs such as vectors. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more "expression control sequences" that control or regulate the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available.

Host cells containing a nucleic acid or vector also are provided herein. Suitable host cells can include, without limitation, bacterial cells, yeast cells, and human or non-human mammalian cells (e.g., HEK 293 cells, 3T3 cells, or HeLa cells).

The fusion polypeptides described herein can include a Cas9 polypeptide sequence and any suitable HUH sequence, which can be derived from any appropriate source. Representative HUH sequences include, without limitation, the amino acid sequences set forth in SEQ ID NOS:1-13. Additional information regarding HUH-containing proteins is found elsewhere (see, e.g., U.S. Publication No. 2016/0340395, which is incorporated herein by reference in its entirety).

SEQ ID NO: 1 (porcine circovirus 2 (PCV2)):
SPSKKNGRSGPQPHKRWVFTLNNPSEDERKKIRDLPISLFDYFIVGEEGN
EEGRTPHLQGFANFVKKQTFNKVKWYLGARCHIEKAKGTDQQNKEYCSKE
GNLLMECGAPRSQGQR SEQ ID NO: 2 (GeneA from PhiX174 Y131H mutant):
KSRRGFAIQRLMNAMRQAHADGWFIVFDTLTLADDRLEAFYDNPNALRDY
FRDIGRMVLAAEGRKANDSHADCYQYFCVPEYGTANGRLHFHAVHFMRTL
PTGSVDPNFGRRVRNRRQLNSLQNTWPYGHSMPIAVRYTQDAFSRSGWLW
PVDAKGEPLKATSYMAVGFYVAKYVNKKSDMDLAAKGLGAKEWNNSLKTK
LSLLPKKLFRIRMSRNFGMKMLTMTNLSTECLIQLTKLGYDATPFNQILK
QNAKREMRLRLGKVTVADVLAAQPVTTNLLKFMRASIKMIGVSNLQSFIA
SMTQKLTLSDISDESKNYLDKAGITTACLRIKSKWTAGGK -continued SEQ ID NO: 3 (mMob mobilization protein from *Escherichia coli*):
MAIYHLTAKTGSRSGGQSARAKADYIQREGKYARDMDEVLHAESGHMPEF
VERPADYWDAADLYERANGRLFKEVEFALPVELTLDQQKALASEFAQHLT
GAERLPYTLAIHAGGGENPHCHLMISERINDGIERPAAQWFKRYNGKTPE
KGGAQKTEALKPKAWLEQTREAWADHANRALERAGH SEQ ID NO: 4 (TraI DNA-nicking and unwinding protein):
MMSIAQVRSAGSAGNYYTDKDNYYVLGSMGERWAGRGAEQLGLQGSVDKD
VFTRLLEGRLPDGADLSRMQDGSNRHRPGYDLTFSAPKSVSMMAMLGGDK
RLIDAHNQAVDFAVRQVEALASTRVMTDGQSETVLTGNLVMALFNHDTSR
DQEPQLHTHAVVANVTQHNGEWKTLSSDKVGKTGFIENVYANQIAFGRLY
REKLKEQVEALGYETEVVGKHGMWEMPGVPVEAFSGRSQTIREAVGEDAS
LKSRDVAALDTRKSKQHVDPEIKMAEWMQTLKETGFDIRAYRDAADQRAD
LRTLTPGPASQDGPDVQQAVTQAIAGLSER SEQ ID NO: 5 (RepB replication protein from *Streptococcus agalactiae*):
MAKEKARYFTFLLYPESIPSDWELKLETLGVPMAISPLHDKDKSSIKGQK
YKKAHYHVLYIAKNPVTADSVRKKIKLLLGEKSLAMVQVVLNVENMYLYL
THESKDAIAKKKHVYDKADIKLINNFDIDRYLE SEQ ID NO: 6 (RepB replication protein from *Streptococcus pneumonia*):
MSEKKEIVKGRDWTFLVYPESAPENWRTILDETFMRWVESPLHDKDVNAD
GEIKKPHWHILLSSDGPITQTAVQKIIGPLNCPNAQKVGSAKGLVRYMVH
LDNPEKYQYSLDEIVGHNGADVASYFELTA SEQ ID NO: 7 (master replication protein from Fava bean necrotic yellow virus (FBNYV)):
MARQVICWCFTLNNPLSPLSLHDSMKYLVYQTEQGEAGNIHFQGYIEMKK
RTSLAGMKKLIPGAHFEKRRGTQGEARAYSMKEDTRLEGPWEYGEFVP SEQ ID NO: 8 (NES nicking protein from *Staphylococcus aureus*):
AMYHFQNKFVSKANGQSAYAKSAYNSASRIKDFKENEFKDYSNKQCDYSE
ILLPNNADDKFKDREYLWNKVHDVENRKNSQVAREIIIGLPNEFDPNSNI
ELAKEFAESLSNEGMIVDLNIHKINEENPHAHLLCTLRGLDKNNEFEPKR
KGNDYIRDWNTKEKHNEWRKRWENVQNKHLEKNGFSVRVSADSYKNQNID
LEPTKKEGWKARKFEDETG SEQ ID NO: 9 (TrwC conjugative relaxase):
MLSHMVLTRQDIGRAASYYEDGADDYYAKDGDASEWQGKGAEELGLSGEV
DSKRFRELLAGNIGEGHRIMRSATRQDSKERIGLDLTFSAPKSVSLQALV
AGDAEIIKAHDRAVARTLEQAEARAQARQKIQGKTRIETTGNLVIGKFRH
ETSRERDPQLHTHAVILNMTKRSDGQWRALKNDEIVKATRYLGAVYNAEL
AHELQKLGYQLRYGKDGNFDLAHIDRQQIEGFSKRTEQIAEWYAARGLDP
NSVSLEQKQAAKVLSRAKKTSVDREALRAEWQATAKELGIDFS SEQ ID NO: 10 (VirD2-T-DNA border endonuclease):
MPDRAQVIIRIVPGGGTKTLQQIINQLEYLSRKGRLELQRSARHLDIPLP
PDQIHELARSWVQETGTYDESQPDEERQQELTTHIIVSFPAGTSQVAAYA
ASREWAAEMFGSGAGGGRYNYLTAFHIDRDHPHLHVVVNRRELLGHGWLK
ISRRHPQLNYDALRIKMAEISLRHGIALDASRRAERGITERPITYAQYRR
LEREQARQIRFEDADLEQSSPQGDHPEFSQPFDTSPFEASAGGPEDMPRP
NNRQNES SEQ ID NO: 11 (replication associated protein for Tomato yellow leaf curl virus (TLYCV)):
MPRLFKIYAKNYFLTYPNCSLSKEEALSQLKKLETPTNKKYIKVCKELHE
NGEPHLHVLIQFEGKYQCKNQRFFDLVSPNRSAHFHPNIQAAKSSTDVKT
YVEKDGNFIDFGVSQIDGRS SEQ ID NO: 12 (RepBm- Plasmid replication protein RepB from *Streptococcus pneumoniae*):
MSEKKEIVKGRDWTFLVYPESAPENWRTILDETFMRWVESPLHDKDVNAD
GEIKKPHWHILLSSDGPITQTAVQKIIGPLNCPNAQKVGSAKGLVRYMVH
LDNPEKYQYSLDEIVGHNGADVASYFELTA SEQ ID NO: 13 (DCV- duck circovirus):
MAKSGNYSYKRWVFTINNPTFEDYVHVLEFCTLDNCKFAIVGEEKGANGT
PHLQGFLNLRSNARAAALEESLGGRAWLSRARGSDEDNEEYCAKESTYLR
VGEPVSKGRSS HUH proteins are endonucleases that can recognize and form stable covalent bonds with specific sequences of unmodified DNA, and the native covalent DNA linking ability of HUH proteins allows for their use to couple DNA to a Cas9 protein, as described herein. Thus, the HUH tags that can be included in the fusion polypeptides described herein can include an HUH endonuclease domain. HUH endonuclease domains are present in many viral replication proteins, relaxases, and transposases.

HUH endonucleases have a small "nicking domain" that, in isolation, can bind and nick specific single-stranded DNA sequences, subsequently forming a covalent link (e.g., a phosphotyrosine ester) between the protein and the 5' end of the DNA strand. The nicking activity of HUH endonucleases typically involves coordinating a metal ion (e.g., a magnesium ion, a nickel ion, or a manganese ion) in the active site by two conserved histidines and a polar residue ("U") that form the catalytic "HUH motif," although it is noted that the HUH motif may contain only one histidine residue. Exemplary metal-coordinating histidine residues are indicated by underlining at residue 57 of SEQ ID NO:1, residues 90 and 92 of SEQ ID NO:2, residues 120 and 122 of SEQ ID NO:3, residues 157 and 159 of SEQ ID NO:4, residues 55 and 57 of SEQ ID NO:5, residue 41 of SEQ ID NO:7, residues 130 and 132 of SEQ ID NO:8, residues 161 and 163 of SEQ ID NO:9, residues 55 and 57 of SEQ ID NO: 11, residues 57 and 59 of SEQ ID NO:12, and residue 52 of SEQ ID NO: 13. The catalytic polar residue of an HUH protein often is a tyrosine residue, but it is noted that any suitable catalytic polar amino acid residue (e.g., serine, threonine, or cysteine) can be used. Exemplary polar catalytic amino acid residues are indicated by italics and underlining at residue 96 of SEQ ID NO:1, residue 128 of SEQ ID NO:2, residue 25 of SEQ ID NO:3, residue 16 of SEQ ID NO:4, residue 99 of SEQ ID NO:5, residue 79 of SEQ ID NO:7, residue 24 of SEQ ID NO:8, residue 26 of SEQ ID NO:9, residue 101 of SEQ ID NO:11, residue 97 of SEQ ID NO: 12, and residue 91 of SEQ ID NO:13.

In some cases, the fusion polypeptides provided herein can include a functional fragment of an HUH polypeptide, where the functional fragment includes the metal-coordinating residue or residues (typically histidine) and the polar amino acid residue of the catalytic motif, as well as sufficient additional amino acids to allow the HUH fragment to possess DNA nicking activity. Exemplary HUH fragments that can be used as tags in the fusion polypeptides provided herein include, without limitation, amino acids 16-99 (with or without a deletion within amino acids 46-55) of SEQ ID NO:1, amino acids 6-126 of SEQ ID NO:3, amino acids 6-101 of SEQ ID NO:5, amino acids 7-94 of SEQ ID NO:7, amino acids 12-98 of SEQ ID NO:12, and amino acids 11-101 of SEQ ID NO:13.

In some cases, an HUH tag can include one or more amino acid sequence modifications with respect to the amino acid sequences provided herein. For example, an HUH tag sequence can include a deletion of one or more amino acid residues (e.g., one or more of amino acids 46-55 of SEQ ID NO:1), or can include an amino acid substitution (e.g., a conservative amino acid substitution). Conservative substitutions for a particular amino acid residue in a reference sequence typically can be selected from other members of the class to which the amino acid residue belongs. For example, an amino acid belonging to a group of amino acids having a particular size or characteristic (such as charge, hydrophobicity, or hydrophilicity) can be substituted for another amino acid within the group, without altering the activity and/or structure of the polypeptide. Examples of amino acid groupings include nonpolar (hydrophobic) amino acids (alanine, leucine, isoleucine, valine, proline, phenylalanine, tryptophan, and tyrosine), polar neutral amino acids (glycine, serine, threonine, cysteine, tyrosine, asparagine, and glutamine), positively charged (basic) amino acids (arginine, lysine, and histidine), and negatively charged (acidic) amino acids (aspartic acid and glutamic acid). Thus, exemplary conservative substitutions include, without limitation, Lys for Arg or Arg for Lys to maintain a positive charge, Glu for Asp or Asp for Glu to maintain a negative charge, Ser for Thr so that a free —OH is maintained, and Gln for Asn to maintain a free $—NH_2$.

In some cases, a fusion polypeptide as provided herein (e.g., a fusion polypeptide containing a Cas9 endonuclease and an HUH tag) can include an HUH tag having the amino acid sequence set forth in any one of SEQ ID NOS:1 to 13. In some cases, a fusion polypeptide can include a functional fragment of any of SEQ ID NOS:1 to 13, where the functional fragment includes an HUH catalytic motif and has the ability to bind to a DNA sequence. In some cases, a fusion polypeptide can include a HUH tag with an amino acid sequence that includes one or more variations (e.g., amino acid deletions, additions, or substitutions) as compared to SEQ ID NOS:1 to 13. Such an HUH tag can have an amino acid sequence that is at least 90% (e.g., at least 92%, at least 95%, at least 97%, at least 98%, at least 99%, 90 to 93%, 93 to 95%, 95 to 98%, or 98 to 99.9%) identical to a sequence as set forth in any of SEQ ID NOS:1 to 13.

A fusion polypeptide described herein (e.g., a fusion polypeptide containing a Cas9 endonuclease and an HUH tag) can include any appropriate Cas9 endonuclease. The Cas9 protein includes two distinct active sites—a RuvC-like nuclease domain and a HNH-like nuclease domain, which generate site-specific nicks on opposite DNA strands (Gasiunus et al., *Proc Natl Acad Sci USA* 109(39):E2579-E2586, 2012). The RuvC-like domain is near the amino terminus of the Cas9 protein and is thought to cleave the target DNA that is noncomplementary to the crRNA, while the HNH-like domain is in the middle of the protein and is thought to cleave the target DNA that is complementary to the crRNA. A representative Cas9 sequence from *Streptococcus thermophilus* is set forth in SEQ ID NO: 14 (see, also, UniProtKB number Q03JI6), and a representative Cas9 sequence from *S. pyogenes* is set forth in SEQ ID NO:15 (see, also, UniProtKB number Q99ZW2).

```
SEQ ID NO: 14 (S. thermophilus):
MTKPYSIGLDIGTNSVGWAVTTDNYKVPSKKMKVLGNTSKKYIKKNLLGV

LLFDSGITAEGRRLKRTARRRYTRRRNRILYLQEIFSTEMATLDDAFFQR

LDDSFLVPDDKRDSKYPIFGNLVEEKAYHDEFPTIYHLRKYLADSTKKAD

LRLVYLALAHMIKYRGHFLIEGEFNSKNNDIQKNFQDFLDTYNAIFESDL

SLENSKQLEEIVKDKISKLEKKDRILKLFPGEKNSGIFSEFLKLIVGNQA

DFRKCFNLDEKASLHFSKESYDEDLETLLGYIGDDYSDVFLKAKKLYDAI

LLSGFLTVTDNETEAPLSSAMIKRYNEHKEDLALLKEYIRNISLKTYNEV

FKDDTKNGYAGYIDGKTNQEDFYVYLKKLLAEFEGADYFLEKIDREDFLR

KQRTFDNGSIPYQIHLQEMRAILDKQAKFYPFLAKNKERIEKILTFRIPY

YVGPLARGNSDFAWSIRKRNEKITPWNFEDVIDKESSAEAFINRMTSFDL

YLPEEKVLPKHSLLYETFNVYNELTKVRFIAESMRDYQFLDSKQKKDIVR

LYFKDKRKVTDKDIIEYLHAIYGYDGIELKGIEKQFNSSLSTYHDLLNII

NDKEFLDDSSNEAIIEEIIHTLTIFEDREMIKQRLSKFENIFDKSVLKKL

SRRHYTGWGKLSAKLINGIRDEKSGNTILDYLIDDGISNRNFMQLIHDDA

LSFKKKIQKAQIIGDEDKGNIKEVVKSLPGSPAIKKGILQSIKIVDELVK

VMGGRKPESIVVEMARENQYTNQGKSNSQQRLKRLEKSLKELGSKILKEN

IPAKLSKIDNNALQNDRLYLYYLQNGKDMYTGDDLDIDRLSNYDIDHIIP

QAFLKDNSIDNKVLVSSASNRGKSDDVPSLEVVKKRKTFWYQLLKSKLIS

QRKFDNLTKAERGGLSPEDKAGFIQRQLVETRQITKHVARLLDEKFNNKK

DENNRAVRTVKIITLKSTLVSQFRKDFELYKVREINDFHHAHDAYLNAVV

ASALLKKYPKLEPEFVYGDYPKYNSFRERKSATEKVYFYSNIMNIFKKSI

SLADGRVIERPLIEVNEETGESVWNKESDLATVRRVLSYPQVNVVKKVEE

QNHGLDRGKPKGLFNANLSSKPKPNSNENLVGAKEYLDPKKYGGYAGISN

SFTVLVKGTIEKGAKKKITNVLEFQGISILDRINYRKDKLNFLLEKGYKD

IELIIELPKYSLFELSDGSRRMLASILSTNNKRGEIHKGNQIFLSQKFVK

LLYHAKRISNTINENHRKYVENHKKEFEELFYYILEFNENYVGAKKNGKL

LNSAFQSWQNHSIDELCSSFIGPTGSERKGLFELTSRGSAADFEFLGVKI

PRYRDYTPSSLLKDATLIHQSVTGLYETRIDLAKLGEG

SEQ ID NO: 15 (S. pyogenes):
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY
```

-continued

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

Thus, the materials and methods provided herein can utilize a Cas9 polypeptide having the sequence of SEQ ID NO:14 or SEQ ID NO:15. In some embodiments, however, the methods described herein can be carried out using a Cas9 functional variant having at least 80% (e.g., at least 85%, at least 90%, at least 95%, or at least 98%) sequence identity with SEQ ID NO: 14 or SEQ ID NO:15. Thus, in some embodiments, a polypeptide (e.g., a fusion polypeptide containing Cas9 and an HUH tag) can contain one or more amino acid substitutions, deletions, or additions as compared to the sequence set forth in SEQ ID NO:14. In certain cases, polypeptides containing such changes can have at least 80% (e.g., at least 85%, 90%, 91%, 92%, 93%, 94%, 95%, 96%, 97%, 98%, or 99%) sequence identity to SEQ ID NO:15. The activity of a functional Cas9 variant may be altered as compared to the corresponding unmodified Cas9 polypeptide. For example, by modifying specific amino acids in the Cas9 protein that are responsible for DNA cleavage, the Cas9 can function as a DNA nickase (Jinek et al., *Science* 337:816-821, 2012), or as a DNA binding protein that has no nuclease or nickase activity but is capable of interacting with DNA to interfere with incoming proteins (Qi et al. *Cell* 152:1173-1183, 2013).

In some embodiments, therefore, a Cas9 protein may not have double-stranded nuclease activity, but may have nickase activity such that it can generate one or more single strand nicks within a preselected target sequence when complexed with a gRNA. For example, a Cas9 polypeptide can have a D10A substitution in which an alanine residue is substituted for the aspartic acid at position 10, resulting in a nickase. In some cases, a Cas9 polypeptide can have an H840A substitution in which an alanine residue is substituted for the histidine at position 840, resulting in a "nuclease-dead" Cas9 that has neither nuclease nor nickase activity, but can bind to a preselected target sequence when complexed with a gRNA. A Cas9 polypeptide also can include a combination of D10A and H840A substitutions, or D10A, D839A, H840A, and N863A substitutions. See, e.g., Mali et al., *Nature Biotechnol,* 31:833-838, 2013.

Amino acid substitutions also can be made by selecting conservative substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of conservative substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. In some embodiments, an amino acid substitution can be non-conservative, such that a member of one of the amino acid classes described above is exchanged for a member of another class.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -l; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -l -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:15), or by an articulated length (e.g., 100 consecutive nucleotides or amino acid residues from a sequence set forth in an identified sequence), followed by multiplying the resulting value by 100. For example, an amino acid sequence that has 1300 matches when aligned with the sequence set forth in SEQ ID NO: 15 is 95 percent identical to the sequence set forth in SEQ ID NO:15 (i.e., 1300÷1368×100=95). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

In some cases, a fusion polypeptide described herein (e.g., a fusion polypeptide containing a Cas9 endonuclease and an HUH tag) can include a second tag (e.g., a protein tag). Examples of protein tags include, without limitation, small ubiquitin-like modifier (SUMO) polypeptides. In cases, where a fusion polypeptide containing a Cas9 endonuclease and an HUH tag also includes a SUMO tag, the fusion polypeptide can include the sequence set forth below.

```
                                        SEQ ID NO: 16
(SUMO-Cas9-NLS-PCV)
MRGSHHHHHHMASGSDSEVNQEAKPEVKPEVKPETHINLKVSDGSSEIFF

KIKKTTPLRRLMEAFAKRQGKEMDSLRFLYDGIRIQADQTPEDLDMEDND

IIEAHREQIGGSMDKKYSIGLDIGTNSVGWAVITDEYKVPSKKFKVLGNT

DRHSIKKNLIGALLFDSGETAEATRLKRTARRRYTRRKNRICYLQEIFSN

EMAKVDDSFFHRLEESFLVEEDKKHERHPIFGNIVDEVAYHEKYPTIYHL

RKKLVDSTDKADLRLIYLALAHMIKFRGHFLIEGDLNPDNSDVDKLFIQL

VQTYNQLFEENPINASGVDAKAILSARLSKSRRLENLIAQLPGEKKNGLF

GNLIALSLGLTPNFKSNFDLAEDAKLQLSKDTYDDDLDNLLAQIGDQYAD

LFLAAKNLSDAILLSDILRVNTEITKAPLSASMIKRYDEHHQDLTLLKAL

VRQQLPEKYKEIFFDQSKNGYAGYIDGGASQEEFYKFIKPILEKMDGTEE

LLVKLNREDLLRKQRTFDNGSIPHQIHLGELHAILRRQEDFYPFLKDNRE

KIEKILTFRIPYYVGPLARGNSRFAWMTRKSEETITPWNFEEVVDKGASA

QSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLKT

YAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGIL

QTVKVVDELVKVMGRHKPENIVIEMARENQTTQKGQKNSRERMKRIEEGI
```

-continued

```
KELGSQILKEHPVENTQLQNEKLYLYYLQNGRDMYVDQELDINRLSDYDV

DHIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSR

MNTKYDENDKLIREVKVITLKSKLVSDFRKDFQFYKVREINNYHHAHDAY

LNAVVGTALIKKYPKLESEFVYGDYKVYDVRKMIAKSEQEIGKATAKYFF

YSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYK

EVKKDLIIKLPKYSLFELENGRKRMLASAGELQKGNELALPSKYVNFLYL

ASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTS

TKEVLDATLIHQSITGLYETRIDLSQLGGDGGGSGTRLPKKKRKVGGGSG

SPSKKNGRSGPQPHKRWVFTLNNPSEDERKKIRDLPISLFDYFIVGEEGN

EEGRTPHLQGFANFVKKQTFNKVKWYLGARCHIEKAKGTDQQNKEYCSKE

GNLLMECGAPRSQGQR
```

The donor DNA used with the HUH-tagged endonuclease in the methods provided herein can be single stranded or can be double stranded but have a single stranded overhang at one or both ends, and can have homology to a particular sequence within the genome of the cells or organism of interest. Typically, a donor DNA includes a nucleic acid sequence that will replace an endogenous target sequence within the cells of interest, flanked by sequences homologous to endogenous sequences on either side of the target. The donor DNA can have a length of about 25 nt to about 500 nt (e.g., 25 to 50 nt, 50 to 100 nt, 100 to 200 nt, 200 to 300 nt, 300 to 400 nt, or 400 to 500 nt). Within the donor DNA, the flanking homologous sequences (also referred to as "homology arms") can have any suitable length (e.g., 5 to 10 nt, 10 to 15 nt, 15 to 20 nt, 20 to 25 nt, 25 to 50 nt, 50 to 75 nt, or 75 to 100 nt). Donor DNA molecules can be obtained commercially or using any suitable technique.

It is noted that endonucleases other than CRISPR/Cas9 systems can be used in the methods provided herein. For example, other endonucleases that can target a particular nucleotide sequence and generate a nick or a double strand break at or near that sequence can be used. Examples of such endonucleases, which are rare-cutting and can be customizable, include zinc finger nucleases (ZFNs), meganucleases (MNs), and transcription activator-like effector (TALE) endonucleases. See, for example, Zhang et al., *Proc Natl Acad Sci USA,* 107(26):12028-12033, 2010; Sander et al., *Nature Methods,* 8:67-69, 2011; Jacoby et al., *Nucl Acids Res,* 10.1093/nar/gkrl303, 2012); Christian et al., *Genetics,* 186:757-761, 2010; U.S. Publication No. 2011/0145940, for discussions of these endonucleases.

This document also provides methods for modifying the genetic material of a cell (e.g., a plant cell, an animal cell, or a bacterial, yeast, or fungal cell). The methods can include introducing into a cell, or a population of cells, a RNP complex that includes (a) a fusion polypeptide containing an HUH tag and an endonuclease or a portion thereof, where the endonuclease is targeted to a selected sequence in the genome of the cell, and (b) a donor DNA that includes a single-stranded target sequence that can specifically interact with the HUH tag. In some cases, the endonuclease can be a Cas9 polypeptide with nuclease or nickase activity, and the RNP also can include a guide RNA that targets the Cas9 polypeptide to a selected target sequence in the genome of the cell. After the RNP complex is introduced into the cells, the RNP complex can interact with the selected sequence (e.g., directed by the guide RNA when the endonuclease is Cas9), the endonuclease can induce a nick or a double strand break at or near the selected sequence, and the donor DNA can be inserted at the nick or double stranded break.

Any suitable method can be used to introduce an RNP complex into a cell. For example, an RNP complex can be delivered by cationic lipid, electroporation, injection, attachment to an antibody, nanobody, or ScFv targeting a cell-surface antigen, attachment to a gold nanoparticle, or attachment to a cell penetrating peptide (also referred to as a protein transduction domains, membrane translocating sequence, or Trojan peptide), a highly cationic, short peptide about 40 amino acids or less in length, that typically is rich in arginine and lysine and has the ability to gain access to the interior of almost any cell.

The invention will be further described in the following example, which does not limit the scope of the invention described in the claims.

EXAMPLE

Methods

Cas9 protein expression: Cas9 was purchased from Integrated DNA Technologies. PCV-Cas9 was constructed by inserting the Cas9 coding sequence between the SUMO and PCV2 proteins at the BamHI site in pTD68_SUMO-PCV2 using Infusion cloning. Cas9-PCV2 were purified according to methods described elsewhere (see, e.g., Anders and Jinek, 2015 *Methods Enzymol* 558:515). Proteins were expressed in *E. coli* BL21(DE3) that were grown in autoinduction media for ~8 hours at 37° C. and then shifted to 25° C. for 24 hours. Cells were collected by centrifugation, resuspended in lysis buffer [20 mM Tris-HCl, pH 8.0, 500 mM NaCl, 5 mM imidazole, 0.4 mM 4-(2-aminoethyl)benzenesulfonyl fluoride hydrochloride (AEBSF)], and lysed by sonication. Soluble protein was bound to Ni-NTA agarose (ThermoFisher), washed with ~15 column volumes lysis buffer, and eluted in 20 mM Tris, pH 8.0, 500 mM NaCl, 500 mM imidazole. The eluate was dialyzed overnight at 4° C. against 20 mM 4-(2-hydroxyethyl)-1-piperazineethanesulfonic acid (HEPES), pH 7.5, 150 mM KCl, 1 mM ethylenediaminetetraacetic acid (EDTA), 1 mM dithiothreitol (DTT), 10% glycerol. The SUMO tag of Cas9-PCV2 was removed with recombinant Ulp1 protease during dialysis. Dialyzed protein was bound to a HiTrap SP HP column (1 mL, GE Healthcare; Wilmington, MA) equilibrated in 20 mM HEPES, pH 7.5, 100 mM KCl, and eluted with a linear KCl gradient from 0.1-1M KCl. Purified protein was snap-frozen in aliquots.

SDS-PAGE of reactions between HUH tags and ssDNA oligos: Unless otherwise noted, gel-shift assays were performed in HUH buffer; 50 mM HEPES pH 8, 50 mM NaCl, 1 mM $MgCl_2$ and 1 mM $MnCl_2$, incubated at 37° C. for 15 minutes unless otherwise noted, and quenched with 4× loading buffer. The reactions were analyzed by electrophoresis on 4-20% polyacrylamide gels and stained with either Coomassie Blue or Bio-Rad Stain-Free gels.

GFP targeting and analysis: GFP knockdown comparison of Cas9 and PCV-Cas9 was performed in a doxycycline inducible GFP cell line made by using In-Fusion HD Cloning (Clontech; Mountain View, CA) to insert GFP into the pLVX-TetOne vector (Clontech). This vector was then used to generate lentiviral particles. HT1080 cells (ATCC; Manassas, VA) were then transduced with lentiviral particles for 48 hours and selected with puromycin in order to generate doxycycline-inducible GFP HT1080 cells. Cells were seeded to ~70% confluency in clear bottom 96-well plates. Ten (10) pmol of Cas9 or PCV2-Cas9 were treated with 50 pmol 3' Cy5 labeled PCV2 target oligo for 5 minutes in OPTI-MEM® (ThermoFisher) supplemented with 1 mM $MgCl_2$. Reactions were split in half and water or 10 pmol GFP single-guide RNA (sgRNA; including a trans-activating crRNA (tracrRNA) and the crRNA) was added for 10 minutes at room temperature. Reactions were split in half and 0.5 µl RNAiMAX (ThermoFisher) was added to half of the reactions for 15 minutes. RNP/liposome mixes were then added to cells in full-media minus antibiotics. Twelve (12) hours later, 1 µM doxycycline was added to wells. Cells were imaged using GFP and Cy5 channels on an EVOS-FL-AUTO 4-10 hours later. Analysis of GFP knockdown and Cy5 intensities was performed in ImageJ.

Cas9-PCV2 transfection and assaying scheme transfection: Cas9-PCV2 ribonucleoproteins were reverse-transfected into HEK293T or U2-OS cells in 96-well format using RNAiMAX (ThermoFisher). The transfection mixture in OPTI-MEM® (ThermoFisher) contained 3-6 pmol Cas9 or Cas9-PCV protein pre-mixed with 3-6 pmol sgRNA for 10 minutes, followed by addition of 3-6 pmol ssODN containing PCV target sequence, 1.2 µl LIPOFECTAMINE™ reagent, and 0.1 mM $MgCl_2$. The mixture was incubated at room temperature for 5-20 minutes in a total volume of 100 µl. Cells were incubated for 48 hours at 37° C., 5% $CO_2$.

Cas9-PCV2 transfection and assaying scheme luminescence assay: Forty-eight hours post-transfection, the cells were washed with PBS, trypsinized, and counted. The cells were centrifuged at 500×g for 5 minutes, and resuspended at $4\times10^5$ cells/mL in growth medium. Twenty thousand (20,000) cells (25 µL) were transferred to a 96 half-well plate (Corning) along with 25 µL of the lytic detection reagent in the NanoGlo HiBiT lytic assay (Promega). The lytic detection reaction contained the luciferin substrate and recombinant protein (LgBiT) corresponding to the portion of split luciferase that will react with the HiBiT tag edited into the genome. The plate was incubated at room temperature for 15 minutes with shaking. Luminescence was assayed using an LMaxII luminometer (Molecular Devices; Sunnyvale, CA) with an integration time of 5 seconds.

Cas9-PCV2 transfection and assaying scheme quantitative PCR: Genomic DNA from transfected cells was purified with the Purelink Genomic DNA mini-kit (ThermoFisher) per the manufacturer's instructions. Quantitative PCR was performed using 2× PowerUp SYBR Green Master Mix (Applied Biosystems; Foster City, CA). The GAPDH/HiBiT locus was amplified using GAPDH primers (Gapdh_F: CTCCCACCTTTCTCATCCAAG (SEQ ID NO:17) and Gapdh_R: ACATCACCCCTCTACCTCC (SEQ ID NO:18)) and HiBiT primers (HiBit_F: GAGACTGGCTCTTAAAAAGTGC (SEQ ID NO:19) and HiBit_R: GCTAATCTTCTTGAACAGCCG (SEQ ID NO:20)). Unmodified gapdh was amplified using gapdh primers. Per reaction, 10 µL of mastermix was combined with 1 µM of each primer, 1 µL gDNA template, and 7 µL nuclease-free water. The two-step qPCR cycling conditions were initial denaturation at 95° C. for 3 minutes, followed by 40 cycles of 95° C. for 15 seconds and 58° C. for 35 seconds. Reactions were performed in triplicate. A method described elsewhere (Livak and Schmittgen; supra) was used to calculate the ratio between Cas9-PCV and Cas9 for HiBiT incorporation, using GAPDH as the reference.

Cas9-PCV2 transfection and assaying scheme deep sequencing assay: A ~200 bp region encompassing a target locus in GAPDH or vinculin was PCR amplified using genomic DNA isolated from transfected HEK293T cells. The GAPDH locus was amplified using primers GAPDH_seq_F (CTGACAACTCTTTTCATCTTCT; SEQ ID NO:21) and GAPDH_seq_R (AAAGTGCAGGGTCTGGCG; SEQ ID NO:22). The vinculin locus was amplified with primers Vinculin_seq_F (ATGAGCTTGCTCCTC CCAAACC; SEQ ID NO:23) and Vinculin_seq_R (TCACTACTTACCTTGCTGGACC; SEQ ID NO:24). Amplicons were gel purified and subsequently ligated to barcoded adaptors. Deep sequencing was performed with an Illumina MiSeq with 2×150 bp paired-end reads (Genewiz Inc., Amplicon-EZ). Sequencing reads were analyzed using CRISPResso (see, e.g., Pinello et al., *Nat Biotechnol* 34:695-697, 2016).

Cas9-PCV2 transfection and assaying scheme off-target analysis: Exonic off-target sites for the GAPDH sgRNA were identified using the CRISPR design tool (Zhang Lab, MIT). Regions surrounding the top four sites were amplified from genomic DNA and sequenced. Tracking of Indel by DEcomposition (TIDE) was employed to identify the indel frequency at each site, using a maximum indel size of 33 bp to account for HiBiT insertion.

Results

Figure 1B:
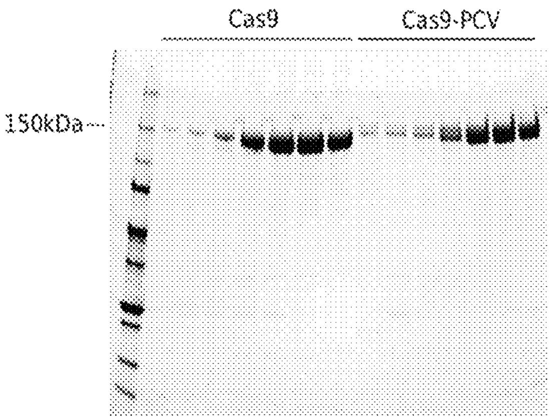
Figure 2:
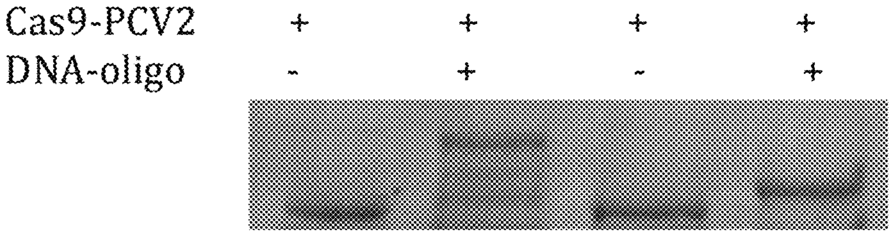
FIG. 2 is an image of an SDS-PAGE gel showing complexes formed between recombinant Cas9-PCV and single stranded DNAs containing the PCV2 target sequence, which forms covalent bonds with the PCV HUH tag, demonstrating in vitro activity. Cas9-PCV2 was reacted in the presence of 0.5 mM $Mg^{++}$ with a long (200 bp) ssODN (lane 2) and a shorter, ~50 bp oligonucleotide (lane 4). Lanes 2 and 4 show bands that run more slowly than the mock conditions (lanes 1 and 3), indicating that a covalent protein-DNA complex has formed and that the HUH tag functions properly when fused to Cas9.

HUH-Cas9 fusions were expressed in *E. coli* in fusion with an N-terminal His6-Sumo domain, and purified using affinity chromatography and cation exchange chromatography (FIG. 1). Reaction of recombinant PCV2-Cas9 with single stranded oligonucleotides bearing their target sequence in the presence of $Mn^{2+}/Mg^{2+}$ resulted in a characteristic covalent adduct, which ran more slowly on SDS-PAGE (FIG. 2). Guide RNA was prepared by in vitro transcription using a kit, or was purchased from IDT (San Jose, CA).

Figure 3A:
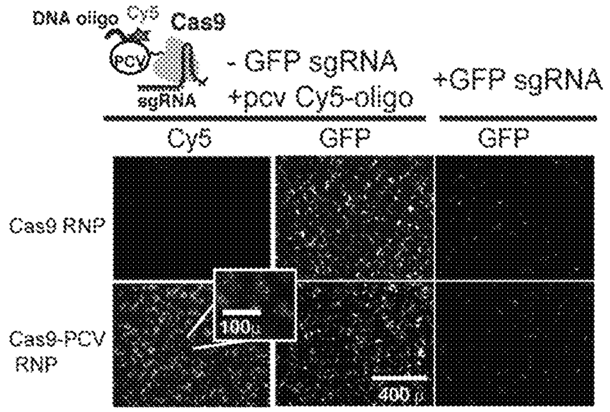
FIGS. 3A and 3B show the results of activity assays, demonstrating that Cas9 can cleave DNA efficiently when fused to an HUH tag. Cas9 or Cas9-PCV was complexed with (1) a gRNA targeted to the GFP locus and designed to interrupt the coding frame of GFP, thus silencing its fluorescence, and (2) an oligonucleotide bearing the PCV2 target sequence conjugated to Cy5 for visualization. The ribonucleoproteins (RNPs) were reverse transfected into an HT1080 cell line stably encoding an inducible GFP. After 12 hours, doxycyclin was added to induce GFP expression. When the Cas9 RNP correctly targeted the GFP locus via its gRNA, double strand breaks occurred, resulting in less GFP fluorescence (FIG. 3A, right panels). GFP fluorescence was read on an EVOS FL-AUTO microscope, and GFP positive cells quantitated using ImageJ. Results are plotted in FIG. 3B, showing a similar loss of GFP fluorescence for both Cas9 and Cas9-PCV when the GFP targeting gRNA was present, demonstrating that Cas9 activity was not affected when the endonuclease was fused to the PCV HUH tag.
Figure 3B:
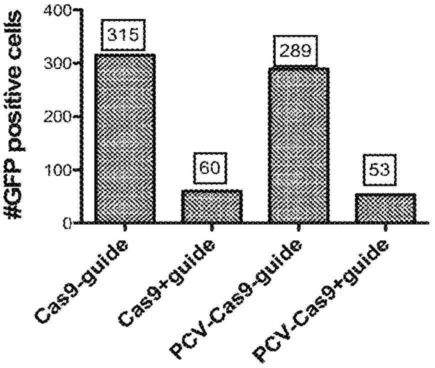

To determine if the Cas9-PCV fusion could induce double stranded breaks as efficiently as Cas9, Cas9 or Cas9-PCV RNPs with a gRNA targeting GFP were delivered to an inducible GFP HCT119 cell line. If Cas9 induced DSBs, the GFP intensity would be decreased. A cationic lipid (LIPOFECTAMINE™ RNAiMAX; ThermoFisher Scientific) was used to deliver 1 pmol Cas9 or Cas9-HUH and 1 pmol GFP gRNA to HCT116 cells stably expressing an inducible GFP. Twelve hours later, GFP expression was induced with doxycycline. After another 12 hours, GFP fluorescence was measured using an EVOS-FL-AUTO fluorescent microscope (ThermoFisher Scientific), and GFP intensity was quantitated using ImageJ. Cas9 and Cas9-PCV caused a similar reduction in GFP fluorescence as compared to the reaction in the absence of the targeting gRNA (FIGS. 3A and 3B).

Figure 4:
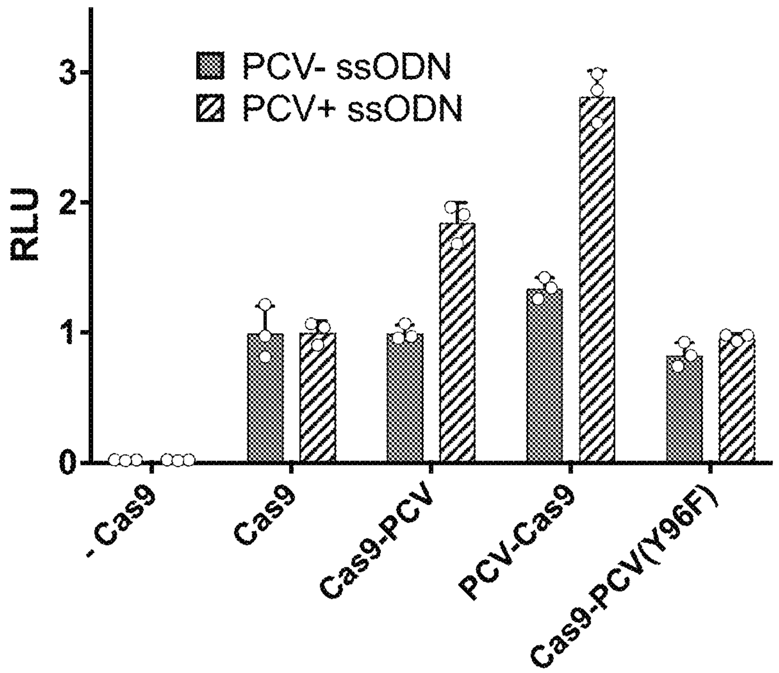
FIG. 4 is a graph showing that tethering of a ssODN to a Cas9-gRNA RNP enhances HDR efficiency. Cas9 was compared to Cas9-PCV fusions for its efficiency in utilizing HDR to incorporate a sequence encoding an 11 amino acid peptide into the endogenous GAPDH gene in HEK293T cells. The 11 amino acid peptide was a split-luciferase tag (e.g., NanoGlo HiBiT lytic assay) that luminesces when the remaining portion of luciferase and luciferase substrate are added (Promega; Madison, WI). The Cas9-PCV fusions contained PCV fused either to the amino terminus (PCV-Cas9) or the carboxyl terminus (Cas9-PCV) of Cas9. A Cas9-PCV mutant (Cas9-PCV(Y96F)) that cannot covalently link to DNA also was tested. Cas9 or the Cas9-PCV fusions were complexed with a gRNA targeted to the 3' end of GAPDH and reacted with a 200 bp ssODN either lacking (PCV-ssODN) or containing (PCV+ssODN) a 5' PCV target sequence to allow covalent tethering to the HUH tag. The complexes were transfected into cells using the cationic lipid LIPOFECTAMINE™ RNAiMAX (ThermoFisher Scientific; Waltham, MA). After 48 hours, the cells were lysed and luciferase reagents were added. Bioluminescence was read on a luminometer in relative light units (RLU).

To determine if tethering of the donor DNA, allowing Cas9, sgRNA, and donor DNA to be delivered as a single complex, has the potential to improve HDR, gene editing was used to insert a small peptide tag at the C-terminus of GAPDH. This peptide tag was part of a split-luciferase system developed by Promega; when the small peptide is incorporated in-frame into GAPDH and reacted with the other portion of the split-luciferase system plus the luciferase substrate, gene-editing can be detected by measuring luminescence. Briefly, a cationic lipid (LIPOFECTAMINE™ CRISPRMAX™; ThermoFisher Scientific) was used to deliver recombinant Cas9 or Cas9-PCV fusions along with sgRNA targeting the C-terminus of GAPDH (purchased from IDT), with or without ssODNs containing the peptide-tag and ~50 bp homology arms±the PCV2 targeting sequence into HEK293T cells. After 48 hours, the cells were lysed, the split-luciferase and luciferase substrate were added, and luminescence was measured. It was consistently observed that the Cas9-PCV fusion coupled with the ssODN containing the PCV2 target sequence to allow covalent coupling resulted in higher levels of luminescence (FIG. 4). Moreover, mutation of the catalytic tyrosine of PCV2, which prevents covalent attachment of the DNA, abrogated the enhancement in luminescence (see, the far right columns of FIG. 4).

Figure 5A:
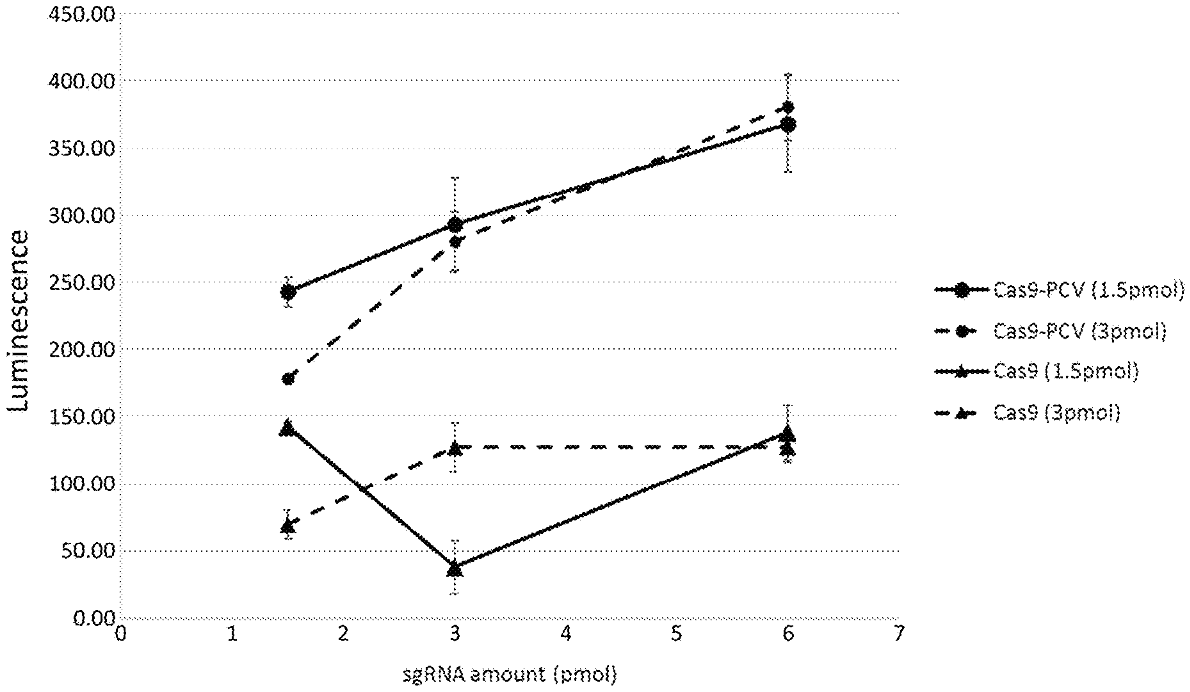
FIGS. 5A and 5B are graphs plotting luciferase activity obtained when the amounts of the RNP components (the Cas9 or Cas9-PCV and the gRNA) were varied. An enhancement of HiBIT incorporation (represented as RLU) was observed when Cas9-PCV was used as compared to Cas9, regardless of concentration. These data indicate that the enhancement is not simply a result of errors in measuring concentrations of the two different proteins.
Figure 5B:
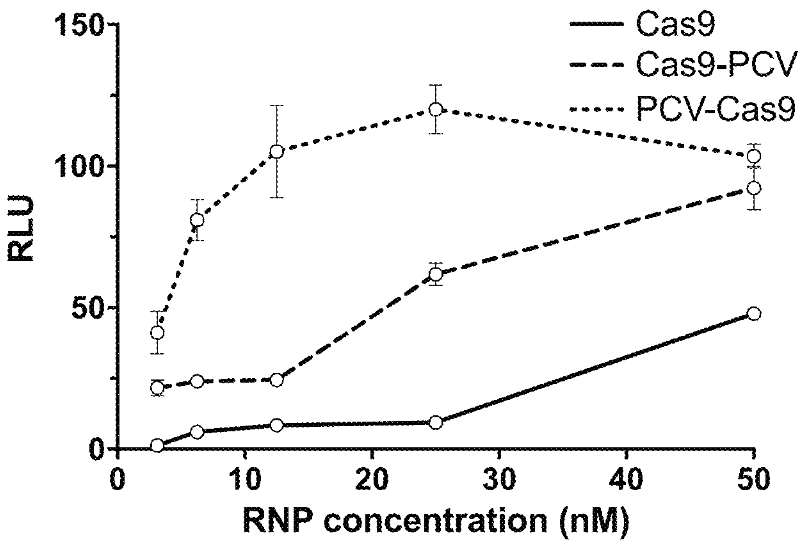

Further experiments were conducted to evaluate the effects of varying the amounts of the RNP components (the Cas9 or Cas9-PCV and the gRNA). As shown in FIGS. 5A and 5B, HiBIT incorporation (represented as RLU) was enhanced when Cas9-PCV fusions were used, as compared to Cas9 alone, regardless of concentration. Thus, the enhancement was not simply a result of errors in measuring concentrations of the two different proteins.

Figure 6A:
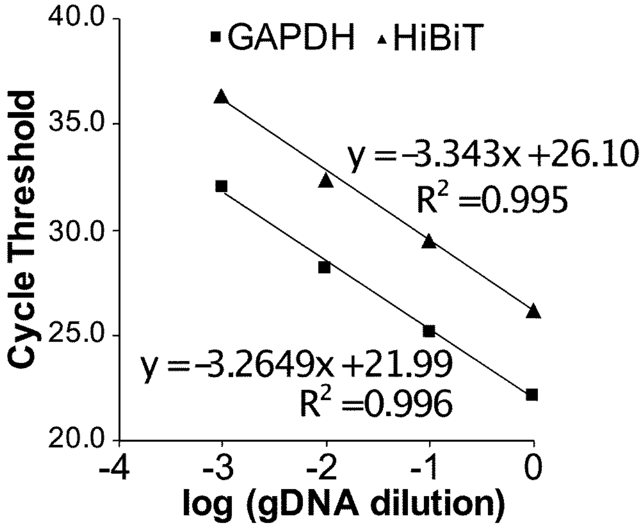
Figure 6C:
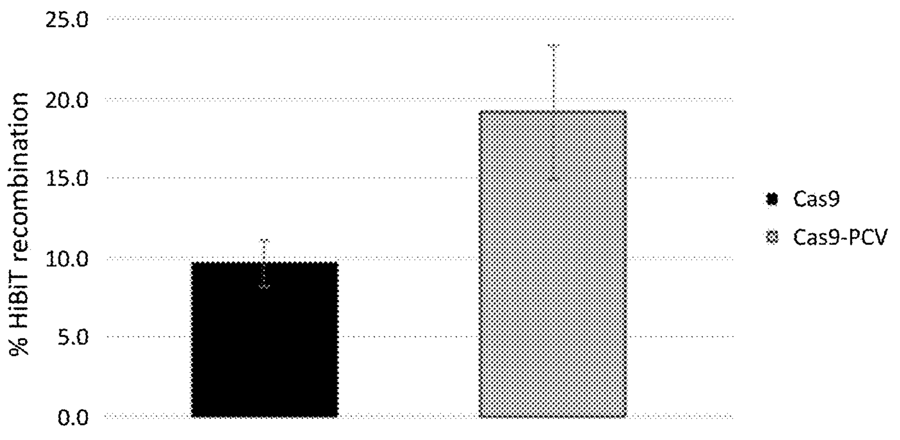

DNA analyses also showed that covalent tethering of the donor DNA to the CRISPR/Cas9 complex enhanced HDR. Quantitative polymerase chain reaction (also referred to as real-time PCR) was performed on cell lysates with two sets of primers—a GAPDH set that annealed to unmodified GAPDH, and a HiBIT set that annealed to luciferase-tag modified GAPDH. The amplification efficiencies of the primers were equivalent (FIG. 6A), demonstrating that the cycle threshold values could be compared. Cycle threshold times are provided in FIG. 6B for triplicate measurements for both sets of primers for PCV or PCV-Cas9. The cycle threshold values were used to calculate the relative incorporation of HiBIT into GAPDH, revealing a two-fold enhancement of HDR efficiency (FIG. 6C) and demonstrating that covalent tethering of the donor DNA to Cas9-PCV enhanced HDR.

Figure 7A:
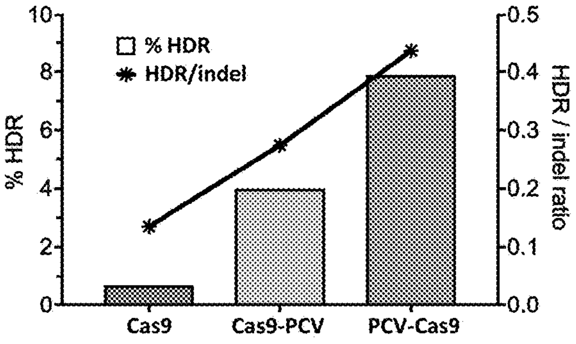
FIGS. 7A and 7B are a graphs plotting absolute HDR efficiencies summarized from deep sequencing results at two different target loci. Cas9 or Cas9-PCV was used to introduce a 33 bp edit in either the GAPDH gene (FIG. 7A) or the vinculin gene (FIG. 7B). The % HDR corresponds to the percentage of sequences that contained the 33 bp insertion. The HDR/indel ratio represents the precise gene editing rate. The fusion of PCV to Cas9 increased both the absolute gene editing efficiency and the precise gene editing ratio.
Figure 7B:
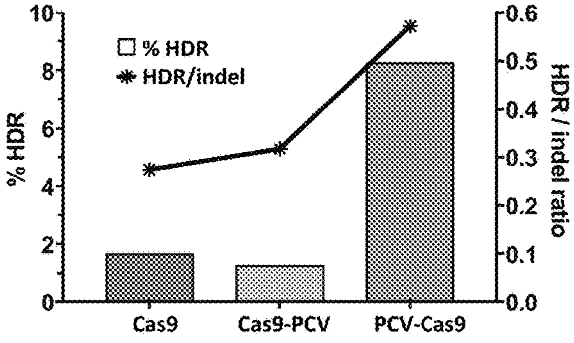

Absolute HDR efficiencies were summarized from deep sequencing results at two different target loci. Cas9 or Cas9-PCV was used to introduce a 33 bp edit in either the GAPDH gene (FIG. 7A) or the vinculin gene (FIG. 7B), and the % HDR was determined. The HDR/indel ratio representing the precise gene editing rate also was determined. These studies showed that fusion of PCV to Cas9 increased both the absolute gene editing efficiency and the precise gene editing ratio.

Figure 8:
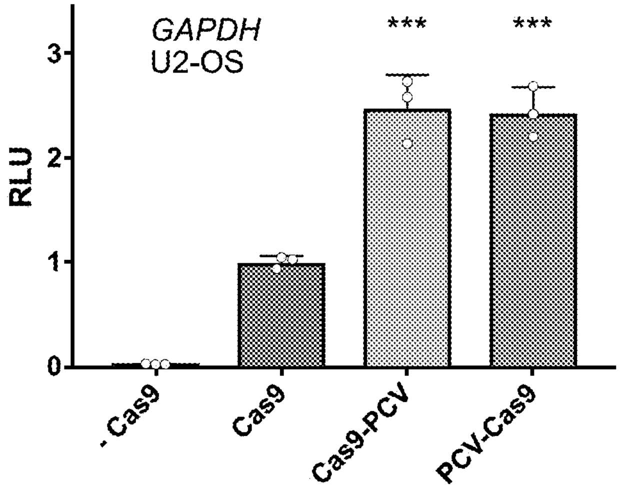
FIG. 8 is a graph plotting the results of inserting the HiBiT tag in U2-OS cells. Luciferase activity was read after targeting the GAPDH locus in U2-OS cells. A significant increase in HDR efficiency was observed when using the Cas9-PCV fusions. Significance was calculated using 2-tailed Student's t test: ***P<0.001.

In additional studies, the HiBiT tag was inserted into the GAPDH gene in U2-OS osteosarcoma cells, and luciferase activity was measured. A significant increase in HDR efficiency was observed when the Cas9-PCV fusions were used, as compared to Cas9 along (FIG. 8; P<0.001).

Figure 9:
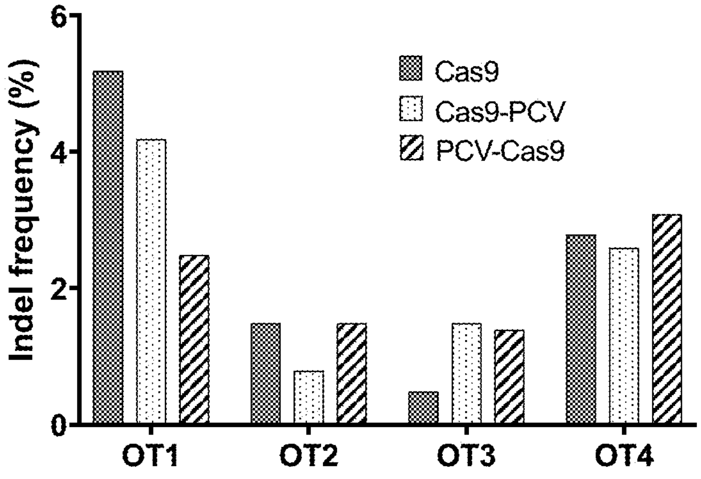
FIG. 9 is a graph plotting the editing rates at the top four exonic off-target (OT) sites of the GAPDH sgRNA. Tracking of Insertion/Deletion by DEcompostion (TIDE) analysis revealed no increase in off-targeting effects due to covalent tethering of the ssODN.

Finally, editing rates at the top four exonic off-target (OT) sites of the GAPDH sgRNA were measured using Tracking of Insertion/Deletion by DEcompostion (TIDE) analysis. No increase in off-targeting effects due to covalent tethering of the ssODN was observed (FIG. 9).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A ribonucleic acid protein (RNP) complex comprising:

(a) a Cas9 endonuclease polypeptide fused to an HUH tag, (b) a donor DNA containing a single-stranded sequence, wherein the donor DNA is covalently attached to the HUH tag, and (c) a guide RNA targeted to a selected sequence in the genome of a cell, wherein the covalent attachment of the donor DNA to the Cas9-HUH fusion polypeptide enhances homology-directed repair (HDR) efficiency compared to Cas9 without covalently attached donor DNA.

2. The RNP complex of claim 1, further comprising a linker between said endonuclease polypeptide and said HUH tag.

3. The RNP complex of claim 1, wherein said HUH tag is fused at the N-terminus of said endonuclease polypeptide.

4. The RNP complex of claim 1, wherein said HUH tag is fused to the C-terminus of said endonuclease polypeptide.

5. The RNP complex of claim 1, wherein said endonuclease polypeptide comprises one or more mutations as compared to a Cas9 endonuclease having the amino acid sequence set forth in SEQ ID NO:14 or SEQ ID NO:15.

6. The RNP complex of claim 5, wherein said one or more mutations reduce the endonuclease activity of said Cas9 endonuclease, reduce non-specific activity of said Cas9 endonuclease, or cause said Cas9 endonuclease to have nickase activity rather than double strand cleavage activity.

7. The RNP complex of claim 1, wherein said HUH tag comprises the amino acid sequence set forth in SEQ ID NO:1.

8. The RNP complex of claim 1, wherein the RNP complex is attached to a gold nanoparticle or is attached to a cell-penetrating polypeptide.

* * * * *